(12) United States Patent
Serebryany et al.

(10) Patent No.: US 10,519,185 B2
(45) Date of Patent: *Dec. 31, 2019

(54) METHODS OF PREPARING SUBSTITUTED NUCLEOSIDE ANALOGS

(71) Applicant: Alios BioPharma, Inc., South San Francisco, CA (US)

(72) Inventors: Vladimir Serebryany, Burlingame, CA (US); Jyanwei Liu, Sunnyvale, CA (US); Leonid Beigelman, San Mateo, CA (US)

(73) Assignee: ALIOS BIOPHARMA, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/905,526

(22) Filed: Feb. 26, 2018

(65) Prior Publication Data

US 2018/0186825 A1   Jul. 5, 2018

Related U.S. Application Data

(63) Continuation of application No. 14/923,283, filed on Oct. 26, 2015, now Pat. No. 9,908,914.

(60) Provisional application No. 62/069,770, filed on Oct. 28, 2014.

(51) Int. Cl.
  *C07H 1/00* (2006.01)
  *C07H 19/06* (2006.01)
  *C07H 23/00* (2006.01)

(52) U.S. Cl.
  CPC .............. *C07H 19/06* (2013.01); *C07H 1/00* (2013.01); *C07H 23/00* (2013.01)

(58) Field of Classification Search
  CPC ........... C07H 23/00; C07H 19/06; C07H 1/00
  See application file for complete search history.

(56) References Cited

U.S. PATENT DOCUMENTS

| | | | |
|---|---|---|---|
| 8,482,021 B2 | 7/2013 | Beigelman et al. | |
| 8,772,474 B2 | 7/2014 | Beigelman et al. | |
| 8,846,896 B2 | 9/2014 | Serebryany et al. | |
| 8,871,737 B2 | 10/2014 | Smith et al. | |
| 8,877,731 B2 | 11/2014 | Beigelman et al. | |
| 8,895,723 B2 | 11/2014 | Serebryany et al. | |
| 8,980,865 B2 | 3/2015 | Wang et al. | |
| 9,012,427 B2 | 4/2015 | Blatt et al. | |
| 9,073,960 B2 * | 7/2015 | Beigelman | C07H 19/00 |
| 9,243,022 B2 | 1/2016 | Beigelman et al. | |
| 9,249,174 B2 | 2/2016 | Beigelman et al. | |
| 9,278,990 B2 | 3/2016 | Smith et al. | |
| 9,346,848 B2 | 5/2016 | Beigelman et al. | |
| 9,365,605 B2 | 6/2016 | Beigelman et al. | |
| 9,394,330 B2 | 7/2016 | Kuldipkumar et al. | |
| 9,422,322 B2 | 8/2016 | Dyatkina et al. | |
| 9,441,007 B2 * | 9/2016 | Wang | A61K 31/7068 |
| 9,504,705 B2 | 11/2016 | Krop et al. | |
| 9,598,457 B2 | 3/2017 | Smith et al. | |
| 9,603,863 B2 | 3/2017 | Blatt et al. | |
| 9,603,864 B2 | 3/2017 | Blatt et al. | |
| 9,605,018 B2 | 3/2017 | Wang et al. | |
| 9,758,544 B2 | 9/2017 | Beigelman et al. | |
| 9,815,864 B2 | 11/2017 | Beigelman et al. | |
| 9,856,284 B2 | 1/2018 | Kuldipkumar et al. | |
| 9,862,743 B2 | 1/2018 | Beigelman et al. | |
| 9,890,188 B2 | 2/2018 | Wang et al. | |
| 9,908,914 B2 | 3/2018 | Serebryany et al. | |
| 9,932,363 B2 | 4/2018 | Dyatkina et al. | |
| 10,052,342 B2 | 8/2018 | Blatt et al. | |
| 10,112,966 B2 | 10/2018 | Beigelman et al. | |

(Continued)

FOREIGN PATENT DOCUMENTS

TW  201343664 A  11/2013
WO  WO 2010/108140  9/2010

(Continued)

OTHER PUBLICATIONS

"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.

(Continued)

*Primary Examiner* — Lawrence E Crane
(74) *Attorney, Agent, or Firm* — Morrison & Foerster LLP

(57) ABSTRACT

Disclosed herein are methods of preparing a nucleoside analog, Compound (I):

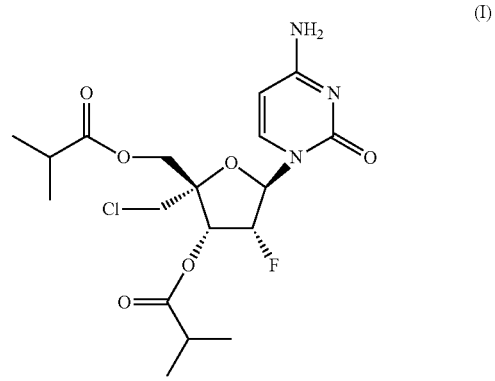

or a pharmaceutically acceptable salt thereof, which is useful in treating diseases and/or conditions such as viral infections, and intermediates thereof.

51 Claims, No Drawings

(56) References Cited

U.S. PATENT DOCUMENTS

| | | |
|---|---|---|
| 10,144,755 B2 | 12/2018 | Beigelman et al. |
| 10,307,439 B2 | 6/2019 | Blatt et al. |
| 10,370,401 B2 | 8/2019 | Beigelman et al. |
| 2010/0048500 A1 | 2/2010 | Cheng et al. |
| 2012/0070411 A1 | 3/2012 | Beigelman et al. |
| 2012/0070415 A1 | 3/2012 | Beigelman et al. |
| 2012/0071434 A1 | 3/2012 | Smith et al. |
| 2012/0165286 A1 | 6/2012 | Beigelman et al. |
| 2013/0164261 A1 | 6/2013 | Wang et al. |
| 2013/0165400 A1 | 6/2013 | Beigelman et al. |
| 2013/0252920 A1 | 9/2013 | Blatt et al. |
| 2013/0253181 A1* | 9/2013 | Serebryany ......... C07F 9/65586 536/26.8 |
| 2013/0281687 A1* | 10/2013 | Serebryany ......... C07F 9/65586 536/28.53 |
| 2014/0179627 A1 | 6/2014 | Beigelman et al. |
| 2014/0179910 A1 | 6/2014 | Beigelman et al. |
| 2014/0303108 A1 | 10/2014 | Beigelman et al. |
| 2014/0303113 A1 | 10/2014 | Krop et al. |
| 2015/0011497 A1 | 1/2015 | Beigelman et al. |
| 2015/0038451 A1 | 2/2015 | Smith et al. |
| 2015/0051167 A1 | 2/2015 | Wang et al. |
| 2015/0105341 A1 | 4/2015 | Beigelman et al. |
| 2015/0141363 A1 | 5/2015 | Wang et al. |
| 2015/0175647 A1 | 6/2015 | Kuldipkumar et al. |
| 2015/0183819 A1 | 7/2015 | Beigelman et al. |
| 2015/0315228 A1 | 11/2015 | Beigelman et al. |
| 2015/0366887 A1 | 12/2015 | Blatt et al. |
| 2015/0366888 A1 | 12/2015 | Blatt et al. |
| 2015/0368286 A1 | 12/2015 | Serebryany et al. |
| 2016/0016987 A1 | 1/2016 | Beigelman et al. |
| 2016/0022724 A1 | 1/2016 | Chanda et al. |
| 2016/0024136 A1 | 1/2016 | Beigelman et al. |
| 2016/0039858 A1 | 2/2016 | Beigelman et al. |
| 2016/0039861 A1 | 2/2016 | Smith et al. |
| 2016/0045528 A1 | 2/2016 | Blatt et al. |
| 2016/0176910 A1 | 6/2016 | Wang et al. |
| 2016/0176911 A1 | 6/2016 | Beigelman et al. |
| 2016/0264610 A1 | 9/2016 | Beigelman et al. |
| 2016/0318967 A1 | 11/2016 | Dyatkina et al. |
| 2016/0318969 A1 | 11/2016 | Kuldipkumar et al. |
| 2016/0331770 A1 | 11/2016 | Beigelman et al. |
| 2017/0002037 A1 | 1/2017 | Beigelman et al. |
| 2017/0037075 A1 | 2/2017 | Beigelman et al. |
| 2017/0037077 A1 | 2/2017 | Beigelman et al. |
| 2017/0143749 A1 | 5/2017 | Blatt et al. |
| 2017/0143751 A1 | 5/2017 | Blatt et al. |
| 2018/0044369 A1 | 2/2018 | Beigelman et al. |
| 2018/0079774 A1 | 3/2018 | Beigelman et al. |
| 2018/0117042 A1 | 5/2018 | Chanda et al. |
| 2018/0155384 A1 | 6/2018 | Wang et al. |
| 2019/0054108 A1 | 2/2019 | Blatt et al. |

FOREIGN PATENT DOCUMENTS

| | | |
|---|---|---|
| WO | WO 2013/142124 | 9/2013 |
| WO | WO 2013/142159 | 9/2013 |
| WO | WO 2013/142525 | 9/2013 |
| WO | WO 2014/100498 | 6/2014 |
| WO | WO 2014/134251 | 9/2014 |
| WO | WO 2014/164533 | 10/2014 |
| WO | WO 2014/209983 | 12/2014 |
| WO | WO 2016/022464 | 2/2016 |
| WO | WO 2018/031818 | 2/2018 |

OTHER PUBLICATIONS

Wang et al., "Discovery of 4'-Chloromethyl-2'-deoxy-3',5'-di-O-isobutyryl-2-fluorocytidine (ALS-81876), A First-in-Class RSV Polymerase Inhibitor for Treatment of Human Respiratory Syncytial Virus Infection" J. Med. Chem. (2015) 58(4):1862-1878.

International Search Report and Written Opinion dated Jan. 265, 2016 for PCT Application No. PCT/US2015/057405 filed Oct. 26, 2015.

International Preliminary Report on Patentability dated May 2, 2017 for PCT Application No. PCT/US2015/057405 filed Oct. 26, 2015.

Office Action dated Aug. 10, 2017 for U.S. Appl. No. 14/923,283, filed Oct. 26, 2015.

Extended Search Report dated Mar. 9, 2018 for EP Application No. 15855437.8, filed Oct. 26, 2015.

Taiwanese Office Action dated Dec. 7, 2018 for TW Application No. 104135489, filed Oct. 28, 2015.

U.S. Appl. No. 16/449,164 filed Jun. 21, 2019 by Wang et al. (Copy not submitted herewith pursuant to the waiver of 37 C.F.R. § 1.98(a)(2)(iii) issued by the Office on Sep. 21, 2004).

U.S. Appl. No. 16/130,971 filed Sep. 13, 2018 by Wang et al. (Copy not submitted herewith pursuant to the waiver of 37 C.F.R. § 1.98(a)(2)(iii) issued by the Office on Sep. 21, 2004).

Taiwanese Notice of Allowance dated Jul. 11, 2019, for TW Application No. 104135489, filed Oct. 28, 2015.

* cited by examiner

METHODS OF PREPARING SUBSTITUTED NUCLEOSIDE ANALOGS

CROSS REFERENCE TO RELATED APPLICATIONS

This application is a continuation application of U.S. patent application Ser. No. 14/923,283, filed on Oct. 26, 2015, now U.S. Pat. No. 9,908,914, which claims priority benefit to U.S. Provisional Application No. 62/069,770, filed on Oct. 28, 2014, the disclosures of which are hereby incorporated by reference in their entireties for all purposes.

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6. For example, each of the following applications are incorporated by reference in their entireties: U.S. application Ser. No. 14/923,283, filed Oct. 26, 2015 and 62/069,770, filed Oct. 28, 2014.

BACKGROUND

Field

The present application relates to the fields of chemistry, biochemistry, and medicine. More particularly, disclosed herein are methods of preparing a nucleoside analog, which can be useful in treating diseases and/or conditions such as viral infections.

Description

Nucleoside analogs are a class of compounds that have been shown to exert antiviral and anticancer activity both in vitro and in vivo, and thus, have been the subject of widespread research for the treatment of viral infections and cancer. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a method of preparing compound (I), or a pharmaceutically acceptable salt thereof.

Other embodiments disclosed herein relate to compound (FF), or a pharmaceutically acceptable salt thereof.

Still other embodiments disclosed herein relate to compound (GG), or a pharmaceutically acceptable salt thereof.

Yet still other embodiments disclosed herein relate to compound (HH), or a pharmaceutically acceptable salt thereof.

DETAILED DESCRIPTION

The synthesis of novel nucleoside analogs often involves several steps. Some of the challenges faced during the synthesis of nucleoside analogs include, but are not limited to, the number of steps, the number and/or amounts of impurities, the amount of chromatography used, the yield for each step, the overall yield, increased purity of an intermediate and/or final product, the crystallinity of each intermediate, the crystallinity of the final product, the number of reagents, the cost of each reagent, the safety of each reagent and the amount and/or toxicity of the waste produced. The aforementioned challenges can increase, and/or further challenges can emerge when a synthesis is scaled-up from a gram scale to a kilogram or more scale. Examples of challenges include the need to confirm one or more intermediates at various steps in the process, a high purity profile and the ability to prepare a substance that flows adequately in large quantities through formulation processing equipment. Therefore, there is a need for one or more for preparing nucleoside analogs that address one or more of these aforementioned challenges.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "halide" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

It is understood that the methods and combinations described herein include crystalline forms (also known as polymorphs, which include the different crystal packing arrangements of the same elemental composition of a compound), amorphous phases and salts.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included, for example, tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compound (I), or a pharmaceutically acceptable salt thereof, is active against a paramyxoviridae virus, such as RSV. An example of a method for forming compound (I), or a pharmaceutically acceptable salt thereof, is shown in Scheme 1.

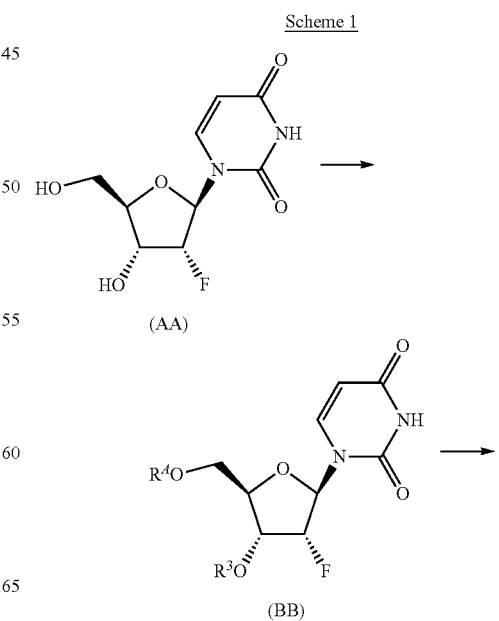

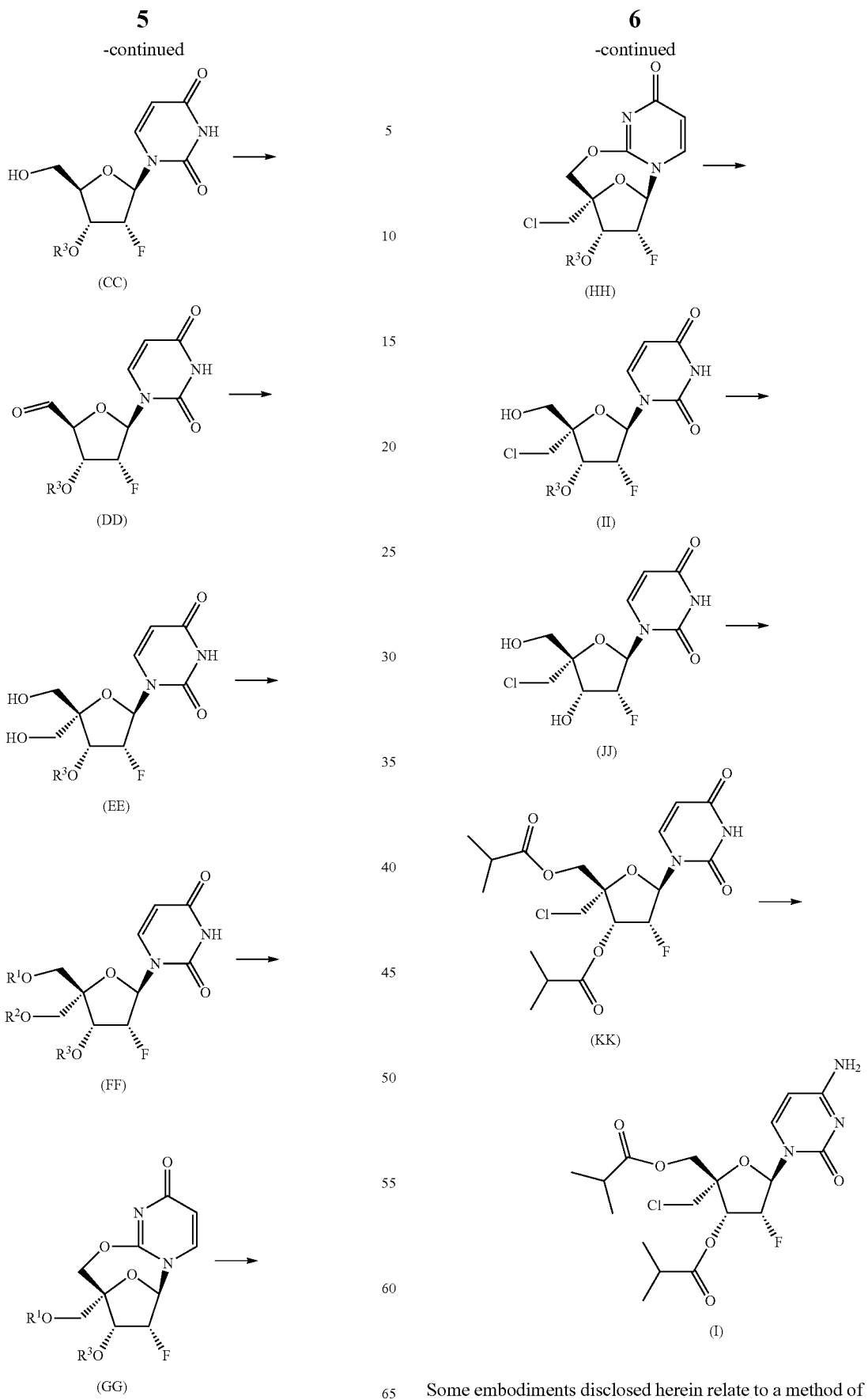
Some embodiments disclosed herein relate to a method of preparing compound (I), or a pharmaceutically acceptable salt thereof, wherein the method can include the use of compound (GG), wherein compound (I) and compound (GG) have the following structures:

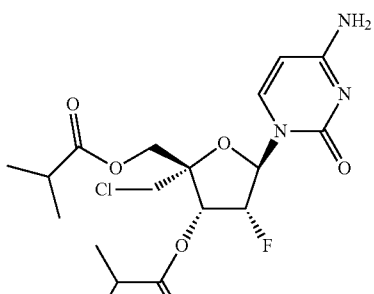

(I)

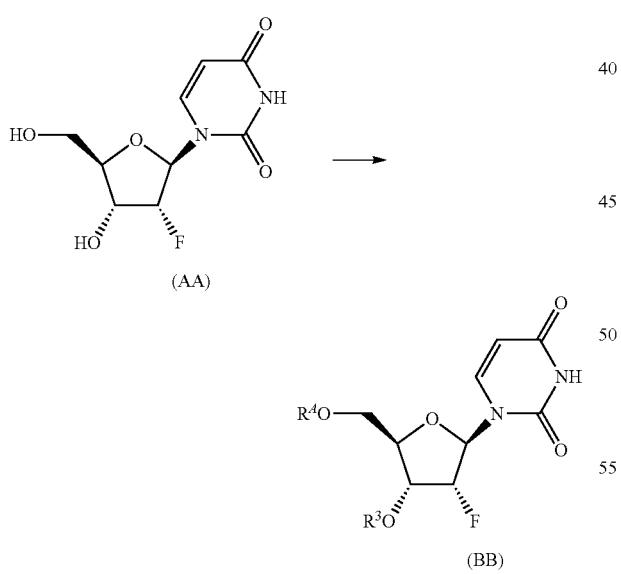

(GG)

wherein: R² can be trifluoromethanesulfonyl (Tf); and R³ can a silyl group or a triarylmethyl group.

In some embodiments, a method described herein can include protecting the 5'-OH group of compound (AA) with a silyl group and the 3'-OH group of compound (AA) with a silyl group or a triarylmethyl group to form compound (BB):

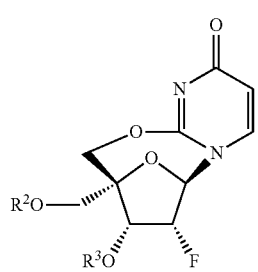

(AA)

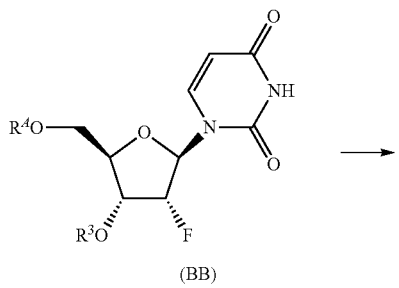

(BB)

wherein: R⁴ can be a silyl group; and R³ can be a silyl group or a triarylmethyl group.

A variety of silyl groups can be used. Examples of silyl groups include, but are not limited to, the following: trimethylsilyl (TMS), triethylsilyl (TES), dimethylisopropylsilyl (IPDMS), diethylisopropylsilyl (DEIPS), tert-butyldimethylsilyl (TBDMS), triisopropylsilyl (TIPS), tert-butyldiphenylsilyl (TBDPS), tri-iso-propylsilyloxymethyl, [2-(trimethylsilyl)ethoxy]methyl, tetraisopropyldisilylene (TIPDS) and di-tert-butyldimethylsilylene (DTBS). When both R⁴ and R³ are silyl groups, the silyl groups can be the same of different. In some embodiments, R⁴ and R³ can each be a triisopropylsilyl group. In some embodiments, the 3'-OH group can be protected using a triarylmethyl group (for example, trityl, monomethoxytrityl (MMTr), 4,4'-dimethoxytrityl (DMTr) and 4,4',4"-trimethoxytrityl (TMTr)). In some embodiments, R³ can be MMTr. In some embodiments, R³ can be a silyl group. In some embodiments, R³ can be triisopropylsilyl (TIPS). The protection of the 3'-OH group and the 5'-OH group can take place in the presence of a base. Examples of bases include, but are not limited to, an optionally substituted amine base, such as an alkylamine (including mono-, di- and tri-alkylamines (for example, monoethylamine, diethylamine, triethylamine and N,N-diisopropylethylamine)), optionally substituted pyridines (such as collidine and 4-diethylaminopyridine (DMAP)) and optionally substituted imidazoles (for example, N-methylimidazole)). The reaction can be conducted in various solvents, for example, DMF and CH₂Cl₂.

In some embodiments, a method described herein can include removing the R⁴ silyl group attached to the 5'-oxygen of compound (BB) to form compound (CC):

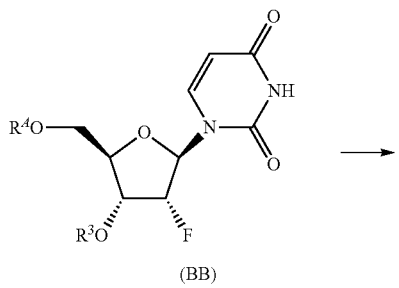

(BB)

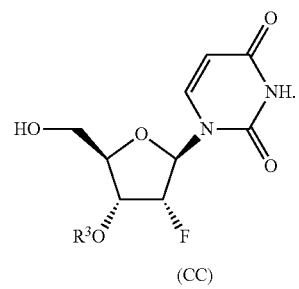

(CC)

As described herein, R⁴ can be a silyl group, such as those described herein. In some embodiments, R⁴ can be a triisopropylsilyl group. The silyl group can be selectively removed using methods known to those skilled in the art. For example, R⁴ can be removed using an acid. The acid can be a mineral acid, such as HCl. The formation of compound (CC) from compound (BB) can be conducted in a polar aprotic solvent(s) (such as, dimethylformamide, dichloromethane, tetrahydrofuran, ethyl acetate, acetone, acetonitrile and/or dimethyl sulfoxide).

In some embodiments, a method described herein can include oxidizing the 5'-OH group of compound (CC) to a 5'-aldehyde group and forming compound (DD):

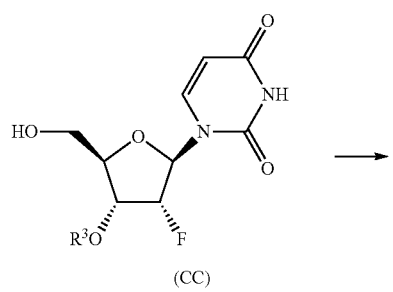

(CC)

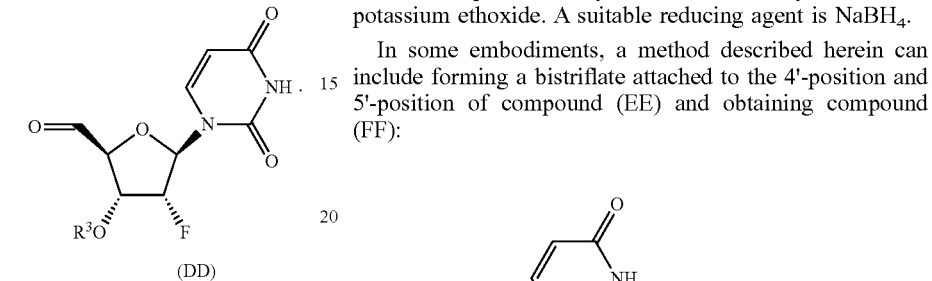

Various suitable oxidizing conditions include, but are not limited to, DMSO in combination with an activating agent (usually an acylating agent or an acid) and an amine base, Moffatt oxidation, Swern oxidation, Corey-Kim oxidation, Pfitzner-Moffatt oxidation, Parikh-Doering oxidation and Anelli's oxidation, and suitable oxidizing agents include, but are not limited to, Dess-Martin periodinane (DMP), TPAP/NMO (tetrapropylammonium perruthenate/N-methylmorpholine N-oxide (Ley oxidation)), a chromium-based reagent (such as Collin's reagent, PCC (pyridinium chlorochromate) and PDC (pyridinium dichromate)), sodium periodate, ceric ammonium nitrate CAN, $Na_2Cr_2O_7$ in water, $Ag_2CO_3$ on celite, hot $HNO_3$ in aqueous glyme, $O_2$-pyridine CuCl, $Pb(OAc)_4$-pyridine, benzoyl peroxide-$NiBr_2$ and 2-iodoxybenzoic acid. In some embodiments, the oxidation conditions can be Swern oxidation conditions.

In some embodiments, a method described herein can include a base catalyzed condensation reaction with formaldehyde and reduction of an aldehyde attached to the 4'-carbon of compound (DD) to form compound (EE):

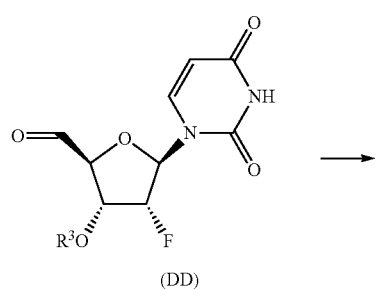

(DD)

A —$CH_2OH$ group can be formed at the 4'-position of compound (DD) using a variety of methods. In some embodiments, formaldehyde can be used to form a —$CH_2OH$ group at the 4'-position via a base catalyzed condensation reaction. An aldehyde attached to the 4'-carbon can be reduced to form the —$CH_2OH$ group of compound (EE). Non-limiting examples of bases include hydroxide, a methoxide, ethoxide and an optionally substituted amine base. Suitable amine base examples are described herein. Additional bases include, but are not limited to, sodium methoxide, potassium hydroxide, sodium hydroxide and potassium ethoxide. A suitable reducing agent is $NaBH_4$.

In some embodiments, a method described herein can include forming a bistriflate attached to the 4'-position and 5'-position of compound (EE) and obtaining compound (FF):

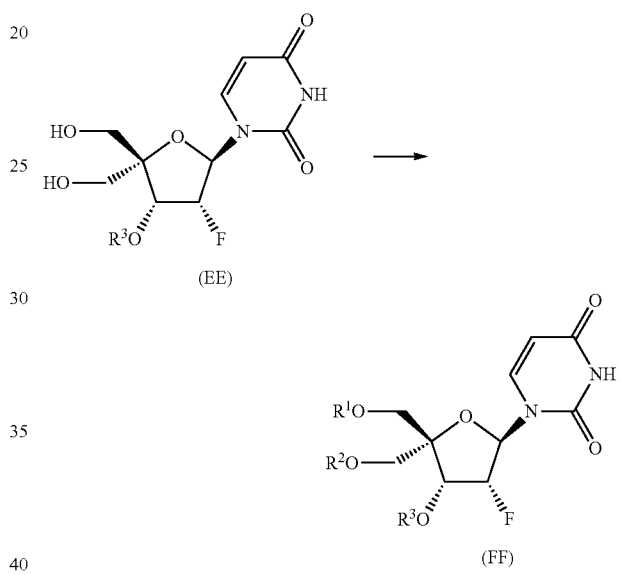

wherein: $R^1$ and $R^2$ are each trifluoromethanesulfonyl (Tf).

Triflic anhydride and/or trifluoromethanesulfonyl halide and optionally a base can be utilized to form the bistriflate. Examples of bases include, but are not limited to, an optionally substituted amine base described herein. In some embodiments, the base can be an optionally substituted pyridine. The formation of compound (FF) from compound (EE) can be conducted in a polar aprotic solvent(s), such as a polar aprotic solvent(s) described herein.

In some embodiments, a method described herein can include cyclizing compound (FF) to form compound (GG):

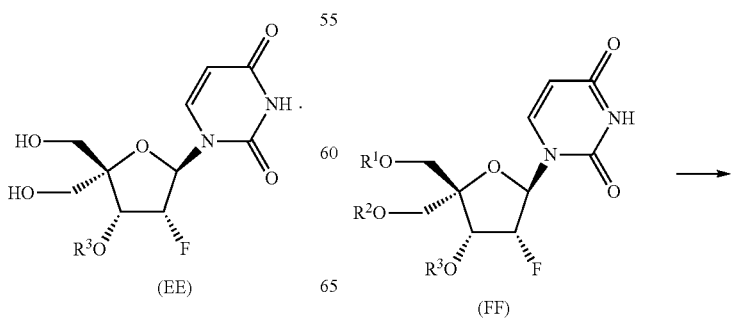

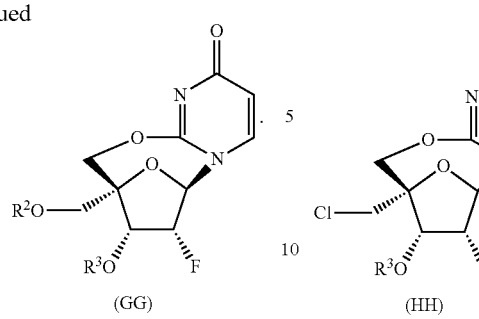

(GG) (HH)

The cyclization reaction forms a 7-membered ring between the uracil base and the 5'-oxygen. The cyclization reaction can be performed in the presence of a base, including those described herein. In some embodiments, the base can be an amine base, such as those described herein. In other embodiments, the base can be an inorganic base, for example, NaH or $K_2CO_3$. In some embodiments, the base can be an amidine reagent. For example, the amidine reagent can be 1,8-diazabicyclo[5.4.0]undec-7-ene (DBU) or 1,5-diazabicyclo[4.3.0]non-5-ene (DBN). The cyclization reaction can be conducted in a polar aprotic solvent(s), for example, a polar aprotic solvent(s) described herein.

In some embodiments, a method described herein can include chlorinating the 4'-position of compound (GG) to form compound (HH):

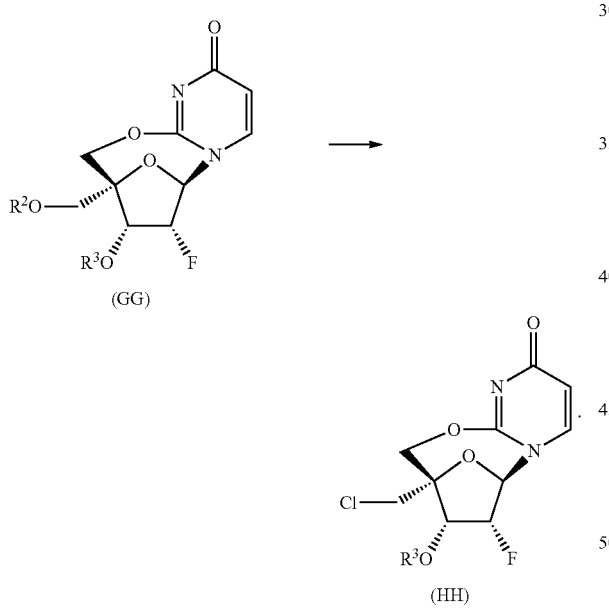

(GG)

(HH)

The $R^2O$ group can be replaced with a chloride group. Various chloride sources can be used, for example, LiCl, CsCl and/or a tetraalkylammonium chloride (such as tetra-n-butylammonium chloride). In some embodiments, the chloride source can be LiCl. The chlorination reaction can take place in a polar aprotic solvent system that can include one or more polar aprotic solvents. In addition to those polar aprotic solvents described herein, the solvent system can include 1,3-Dimethyl-3,4,5,6-tetrahydro-2(1H)-pyrimidinone (DMPU). In some embodiments, the solvent system can be DME-DMPU.

In some embodiments, a method described herein can include cleaving the 7-membered ring of compound (HH) via a hydrolysis reaction to form compound (II):

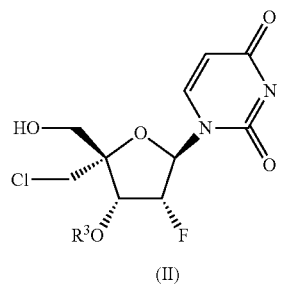

(II)

The 7-membered ring can be opened using an acid or a base. In some embodiments, the acid can be a mineral acid, for example, HCl, diluted sulfuric acid and/or phosphoric acid. In addition or in the alternative, the acid can be an ion-exchange resin in $H^+$ form, such as those known to those skilled in the art. As described herein, a base can be used to cleave the 7-membered ring and provide compound (II). For example, the base can be diluted aqueous sodium hydroxide or similar base.

In some embodiments, a method described herein can include removing the silyl group attached to the 3'-oxygen of compound (II) to form compound (JJ):

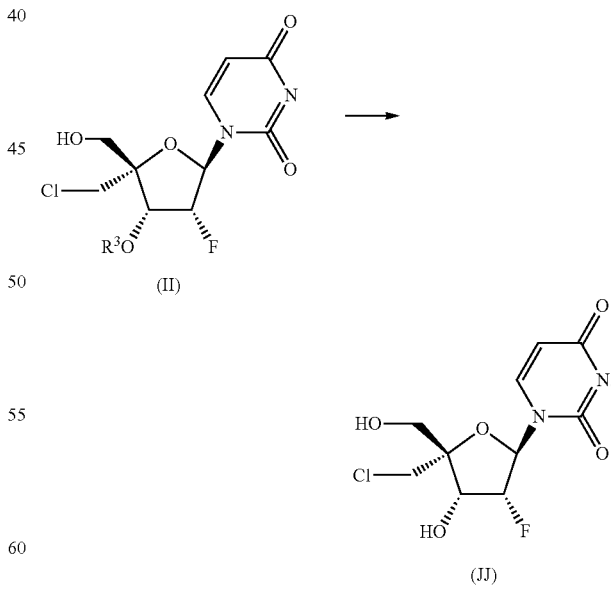

(II)

(JJ)

The silyl group ($R^3$) can be removed using a fluoride source. A non-limiting list of fluoride sources include tetrabutylammonium fluoride (TBAF), pyridine.HF, triethylamine trihydrofluoride, hydrofluoric acid, tris(dimethylamino)

sulfonium difluorotrimethylsilicate (TASF), SiF$_4$ and ammonium fluoride. In some embodiments, the fluoride source can be TBAF.

In some embodiments, a method described herein can include forming an acyl group at each of the 3'-position and the 5'-position of compound (JJ) to form compound (KK):

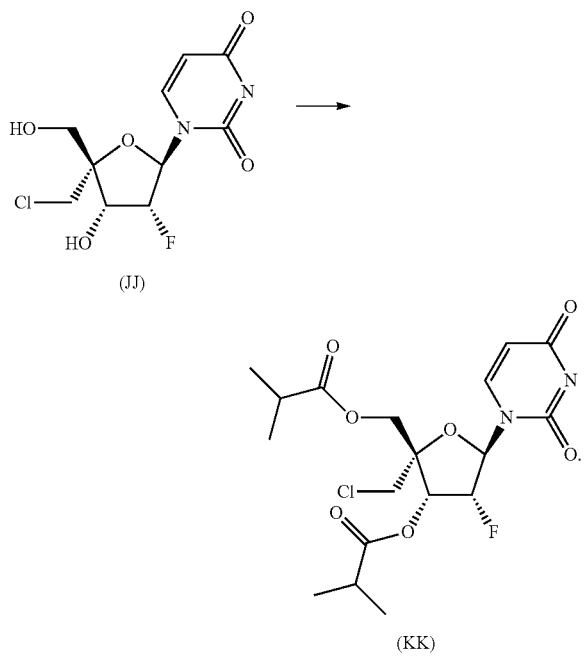

The acyl groups can be forming at the 3'-position and 5'-position of compound (JJ) via an esterification reaction using an acyl anhydride or an acyl chloride, and a nucleophilic catalyst. In some embodiments, the acyl anhydride can be isobutyric anhydride. In some embodiments, the nucleophilic catalyst can be a base. Suitable bases are described herein. In some embodiments, the base can be an amine base, for example, an amine base described herein. In some embodiments, the base can be 4-dimethylaminopyridine (DMAP). In other embodiments, the base can be pyridine. The formation of compound (JJ) from compound (KK) can be conducted in a polar aprotic solvent(s), such as a polar aprotic solvent(s) described herein. In some embodiments, the polar aprotic solvent can be acetonitrile.

In some embodiments, a method described herein can include converting the uracil of compound (KK) to a cytosine and forming compound (I):

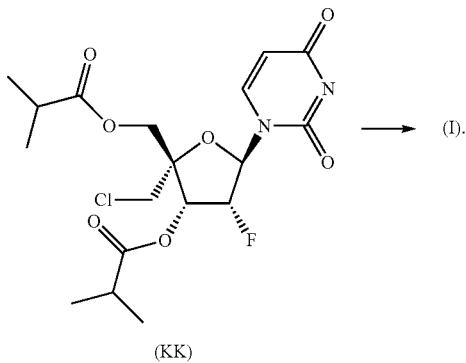

A sulfonate can be formed at the 4-position of the uracil base. Methods for forming a sulfonate are known to those skilled in the art, for example, using a sulfonyl halide. A non-limiting list of sulfonyl halides includes an optionally substituted phenylsulfonyl chloride (for example, tosyl chloride and 2,4,6-triisopropylbenzenesulfonyl chloride) and alkylsulfonyl chloride (such as methanesulfonyl chloride). In some embodiments, the sulfonyl halide can be 2,4,6-triisopropylbenzenesulfonyl chloride. In some embodiments, a catalyst can be used for forming the sulfonate. An example of a suitable catalyst is 4-dimethylaminopyridine (DMAP). The cytosine base can be obtained via an aminolysis of the 4-sulfonate to obtain compound (I). A variety of amination regents are known to those skilled in the art. In some embodiments, the amination regent can be ammonia reagent (NH$_3$.H$_2$O).

In some embodiments, compound (I) can be purified using a suitable solvent system. In some embodiments, the solvent system can be isopropyl acetate (IPAC) and heptane. In other embodiments, the solvent system can be heptane with one or more of the following: ethyl acetate, MTBE, ethanol and/or isopropanol. In still other embodiments, the solvent system can be an aqueous mixture of alcohols (such as methanol, ethanol and/or isopropanol). In yet still other embodiments, the solvent system can be aqueous acetonitrile and/or acetone. After purification, in some embodiments, the purity of compound (I), or a pharmaceutically acceptable salt thereof, can be in the range of 99% to 100%.

The methods described herein can be used to obtain compound (I), or a pharmaceutically acceptable salt thereof, on the scale of several grams. In some embodiments, the methods described herein can be used to obtain at least 25 grams of compound (I), or a pharmaceutically acceptable salt thereof.

In some embodiments, R$^3$ cannot be monomethoxytrityl (MMTr). In some embodiments, R$^3$ cannot be a triarylmethyl group.

Various advantages of a method described herein are provided. In some embodiments, a method described herein can reduce the amount of one or more impurities compared to the amount of one or more impurities produced from a previously utilized method. For example, the amount of an impurity can be reduced in the range of about 1.5-fold to about 10-fold. In some embodiments, the purity of compound (I), or a pharmaceutically acceptable salt thereof, can be greater compared to the purity of compound (I), or pharmaceutically salt thereof, from a previously described method. In some embodiments, compound (I), or a pharmaceutically acceptable salt thereof, can be obtained from compound (A1) without the use of chromatography. In some embodiments, the crystallinity of one or more intermediates and/or compound (I), or a pharmaceutically acceptable salt thereof, can be increased compared to the crystallinity of the same compound obtained from a previously described method. In some embodiments, a method described herein can have improved bulk density of a compound, and therefore, can enhance the flowability of the material in the formulation process compared to the bulk density of the same compound prepared using a method previously described. In some embodiments, a method described herein can proceed without verifying the structure of one or more intermediates while maintaining a high purity profile (for example, percentage of impurities in the range of <5% to 0%)). This can be advantageous because of improved overall efficiency.

EXAMPLES
Additional embodiments are disclosed in further detail in the following examples, which are not in any way intended to limit the scope of the claims.
Example 1
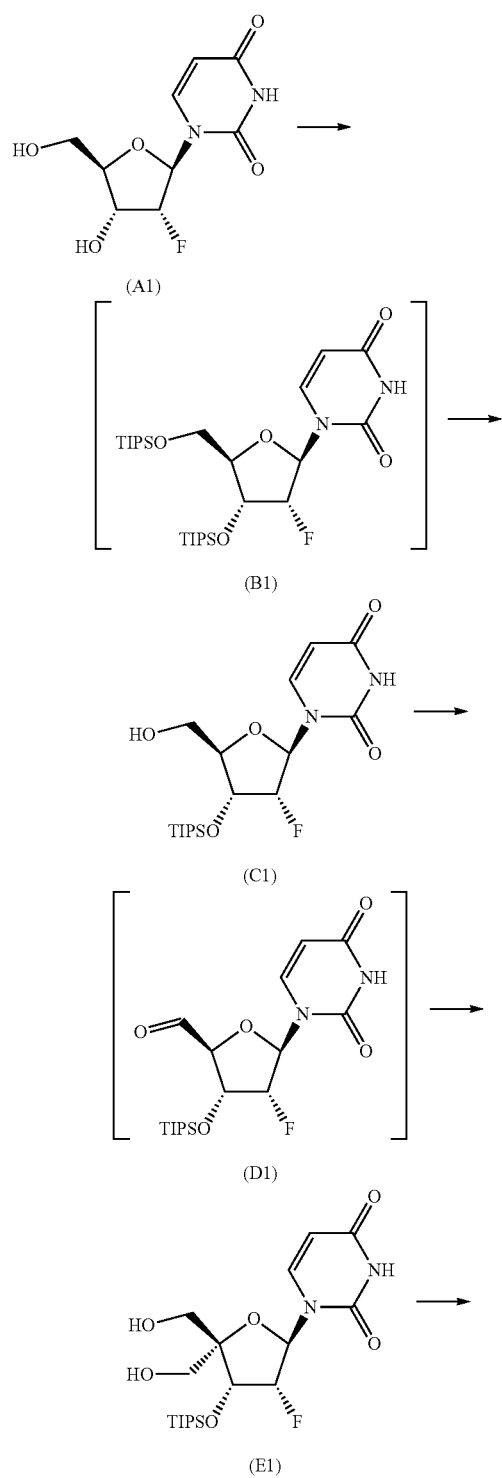
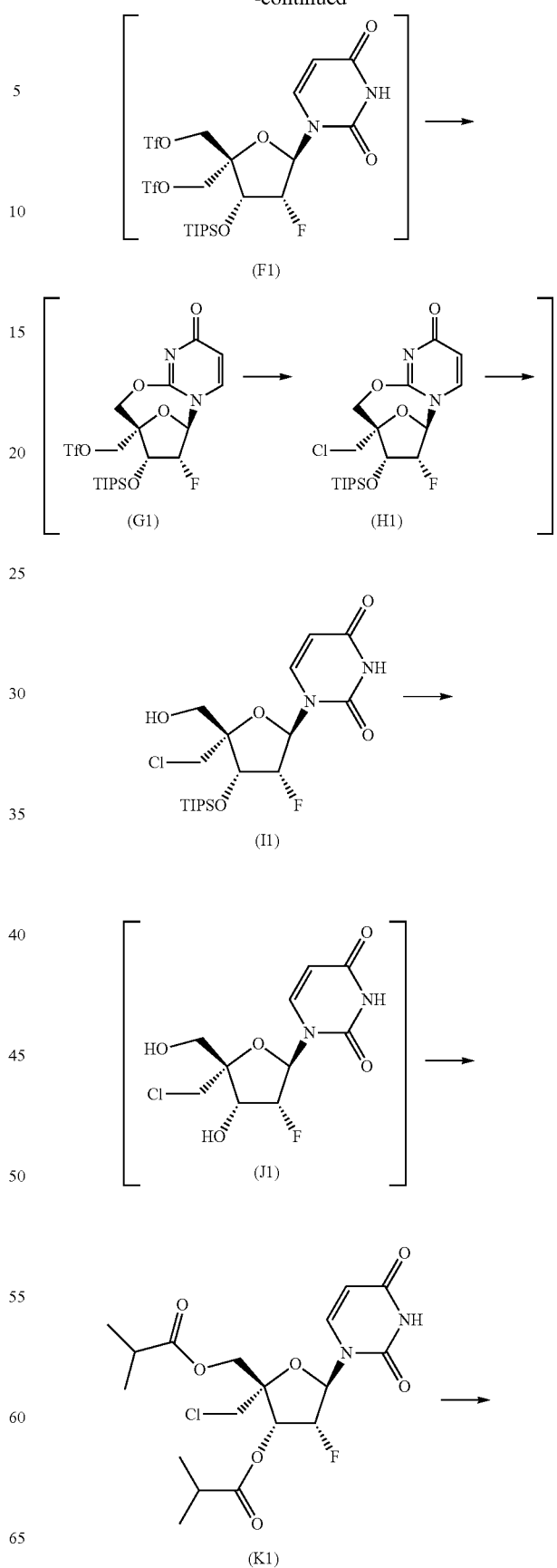

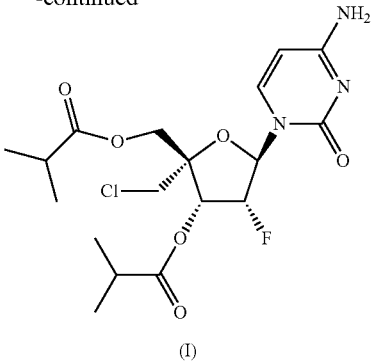

(I)

To compound (A1) (49.9 Kg, 202.7 mol) was added imidazole (66.5 Kg, 976.8 mol) and DMF (129.0 Kg). Triisopropylsilyl chloride (97.8 Kg, 507.3 mol) under nitrogen was added at 30° C. The mixture was stirred at 55-60° C. for 20 h, and then cooled to 15° C. Isopropyl acetate (306.0 Kg) was added, followed by 2N HCl (224 Kg) to reach pH 6 while maintaining the internal temperature below 15° C. The organic layer was washed with 10% brine solution (226 Kg, 2×) at 20° C. To the organic layer was added DMF (245 Kg). The mixture was vacuum distilled at 45° C. until about 400 L of solution was left in the reactor. To the solution was added acetonitrile (480 Kg) and 6N HCl (25.5 Kg). The mixture was stirred at 25° C. for 9 h. A 7% NaHCO$_3$ solution (220.0 Kg) was added to pH 6 and then water (1298 Kg) was added. The precipitate was collected and washed with water to give a wet cake (138.8 Kg). The wet cake was dried at 55-60° C. to give compound (C1) (65.6 Kg, 100.7% by assay, 80% yield in 2 steps).

To a solution of oxalyl chloride (34.0 Kg, 267.9 mol) in DCM (1847 Kg) was added DMSO (44.4 Kg, 568.3 mol) at −75° C. The mixture was stirred at −75° C. for 2 h, and then a solution of compound (C1) (71.0 Kg, 202.7 mol) in THF (229.9 Kg) was added. The mixture was stirred for 2 h, and then triethylamine (62.1 Kg, 613.7 mol) added at −75° C. The mixture was warmed to −55° C. and stirred for 2 h. This mixture was added to a solution of NaH$_2$PO$_4$ (67.1 Kg) dissolved in water (676 Kg) at 0° C. The organic layer was washed with water (700 Kg), and the organic layer was vacuum distilled at 40° C. to reduce the volume to half. 1,4-dioxane (250.6 Kg) was added, and then the mixture was cooled to 10° C. A 37% formaldehyde solution (77.6 Kg) was added, followed by a 2N NaOH solution (261 Kg) while keeping internal temperature below 20° C. NaBH$_4$ (6.7 Kg) was added, and the mixture was stirred for 5 h. A NH$_4$Cl solution (710 Kg) and isopropyl acetate (1210 Kg) were added. The organic layer was washed sequentially with 7% NaHCO$_3$ (710 Kg), water (164 Kg) and 25% brine solution (160 Kg). The organic layer was concentrated, and then n-heptane (548 Kg) was added. The precipitate was collected to give a wet cake (109.4 Kg), which was dried at 45° C. to give compound (E1) (55.5 Kg, 88.2% assay, 65% in 2 steps).

To a solution of compound (E1) (59.0 Kg, 136.4 mol) and pyridine (54.4 Kg) in DCM (730 Kg) was added trifluoromethanesulfonic anhydride (86.1 Kg, 305.2 mol) at −20° C., and the mixture was stirred for 2 h. Water (136 Kg) was added, and the mixture was stirred for 30 mins. 1N HCl (330 Kg) was added, and the organic layer was washed with water (550 Kg, 2×). The organic layer was filtered through a pad of silica gel (60 Kg), and washed with DCM. The filtrate was concentrated to ~180 L in volume, and DME (157 Kg) was added. The mixture was concentrated again until ~180 L of a solution of compound (F1) (27.2 Kg by assay, 39 mol) was left in the reactor.

To this solution from the previous step was added DME (300 Kg) and DBU (7 Kg). The mixture was stirred at 20° C. for 1 h. DMPU (14.6 Kg) was added followed by LiCl (5.0 Kg, 118.2 mol). The mixture was stirred for 15 h. A 2N HCl solution (8.0 Kg) was added, and the mixture was stirred at 25° C. for 1 h. Isopropyl acetate (354 Kg) and water (82 Kg) were added. The organic layer was washed with water (82 Kg, 3×) and then concentrated at 40° C. to ~80 L in volume. Isopropyl acetate (54.4 Kg) was added, and the mixture was stirred for 1 h. N-heptane (160.8 Kg) was added, and the mixture was stirred at 0° C. for 1 h. The precipitate was collected and dried at 60° C. to give compound (I1) (12.3 Kg, 95.5% assay, 54% yield in 4 steps).

To a solution of compound (I1) (42.4 Kg, 94.0 mol) in THF (267 Kg) was added 1M solution of n-Bu$_4$NF in THF (68.0 Kg). The mixture was stirred at 25° C. for 6 h, and then concentrated at 40° C. to ~80 L in volume. Acetonitrile (140 Kg) was added, and the mixture was cooled to 5° C. Triethylamine (28.6 Kg) and DMAP (1.15 Kg) were added. Isobutyric anhydride (33.0 Kg) was then added under 30° C., and the mixture was stirred for 4 h. Glacial acetic acid (7.0 Kg), water (684 Kg) and DME (157 Kg) were added. The mixture was concentrated until ~180 L of a solution of compound (K1) (27.2 Kg by assay, 39 mol) was left in the reactor. The precipitate was collected and dried to give compound (K1) (38.95 Kg, 98.1% assay, 93% yield).

To a solution of compound (K1) (38.2 Kg, 87.8 mol), DMAP (11.5 Kg) and triethylamine (19.1 Kg) in acetonitrile (181 Kg) was added triisopropylbenzenesulfonyl chloride (30.1 Kg) at 10° C. The mixture was stirred at 25° C. for 5 h, and then 25% ammonium hydroxide (13.0 Kg) was added. The mixture was stirred for 3 h, and then water (180 Kg) was added. The precipitate was collected, re-dissolved in isopropyl acetate (490 Kg) and washed with a 7% NaHCO$_3$ solution (169 Kg, 2×). The organic layer was washed sequentially with a 15% NH$_4$Cl (80 Kg) and water (200 Kg). The organic layer was then concentrated to ~220 L in volume. N-heptane (240 Kg) was added. The precipitate was collected and dried to give compound (I) (crude, 26.85 Kg, 101.1% assay, 71% yield).

Procedure A: A solution of compound (I) (crude, 26.9 Kg) in isopropyl acetate (165 Kg) was stirred at 60-70° C. The solution was polish-filtered to a crystallization tank. To this solution was seeded compound (I) (30 g), and the mixture was stirred at 55° C. N-heptane (160 Kg) was added, and the mixture was cooled to 25° C. Crystalline compound (I) was collected and dried to give compound (I) (25.66 Kg, 99.0% assay, 94% yield) as the final product.

Procedure B: A solution of compound (I) (crude, 1.10 Kg) in methanol and purified water (9:1 volume, 6480 g) was stirred at 20-25° C. The solution was filtered to a crystallization tank. To this solution was seeded compound (I) (micronized, 27.3 g), and the mixture was stirred at 20° C. A mixture of purified water and methanol (9:1 volume, 8613 g) was added, and the solution was cooled to 5° C. Crystalline compound (I) was collected and dried in vacuum at 30° C. to give compound (I) (1084 g, 99.7% assay, 95.4% yield) as the final product.

Compound (I) was prepared using the process described in U.S. Pat. No. 9,073,960 on a scale of 2-3 grams (referred to hereinafter as "small-scale"), and using a method described herein, using Procedure A, on a scale of 25 grams (referred to hereinafter as "large-scale"). In the large-scale procedure, compound (I) was prepared without confirming the intermediates formed using chromatography.

Samples from each of the small-scale and large-scale synthetic routes were analyzed by High Performance Liquid Chromatography (HPLC) to quantify the amount of impurities present. The purity profile for each impurity is provided in Table 1.

TABLE 1

|  | Small-Scale (n = 2) | Large Scale |
|---|---|---|
| Impurity 1 | 0.7% | Not detected |
| Impurity 2 | 0.11% | Not detected |
| Impurity 3 | 0.09% | Not detected |
| Impurity 4 | 0.14% | 0.03% (4-fold reduction) |
| Impurity 5 | 0.17% | 0.02% (8-fold reduction) |
| Impurity 6 | 0.05% | 0.03% (1.8-fold reduction) |
| Purity of Compound (I) | 99.4% | 99.9% |

As provided in Table 1, the amount of all six impurities was reduced using a method described herein. In addition, the purity of compound (I) was increased to 99.9%.

The bulk density of Compound (I) prepared using a method described herein was measured using a method provided by the U.S. Pharmacopeia (USP) on a smaller scale (10 mL graduated cylinder). The resulting crystallinity of Compound (I) and its intermediates was enhanced. The crystallinity of Compound (I) was increased in the range of 20% to 60% (comparing small-scale to large-scale). As a result, the need for chromatography to confirm the presence of the appropriate compound at various steps of the process was unnecessary. Moreover, the enhanced bulk density of Compound (I) improves its flowability in formulation processes.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of preparing a compound of formula (I):

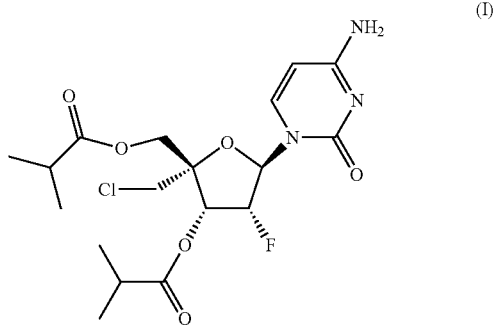 [SMILES: CC(C)C(=O)OC[C@@]1(CCl)O[C@@H](n2ccc(N)nc2=O)[C@H](F)[C@@H]1OC(=O)C(C)C]

or a pharmaceutically acceptable salt thereof, comprising:
forming a sulfonate at the 4-position of the uracil base of a compound of formula (KK); and converting the sulfonate to the compound of formula (I), or a pharmaceutically acceptable salt thereof, via aminolysis; wherein the compound of formula (KK) is:

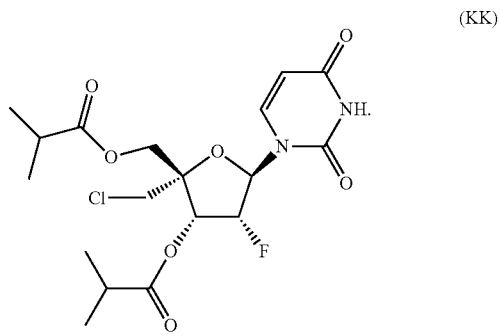 [SMILES: CC(C)C(=O)OC[C@@]1(CCl)O[C@@H](n2ccc(=O)[nH]c2=O)[C@H](F)[C@@H]1OC(=O)C(C)C]

2. The method of claim 1, further comprising:
preparing the compound of formula (KK) by esterifying a compound of formula (JJ) to provide the compound of formula (KK), wherein the compound of formula (JJ) is:

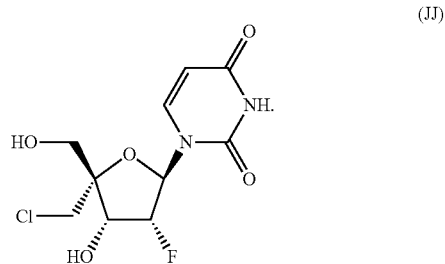 [SMILES: O=c1ccn([C@@H]2O[C@@](CO)(CCl)[C@@H](O)[C@H]2F)c(=O)[nH]1]

3. The method of claim 2, wherein the compound of formula (JJ) is esterified by contacting the compound of formula (JJ) with isobutyric anhydride.

4. The method of claim 2, further comprising adding 4-dimethylaminopyridine as a catalyst.

5. The method of claim 2, further comprising preparing the compound of formula (JJ) by removing the $R^3$ group of a compound of formula (II), wherein the compound of formula (II) is:

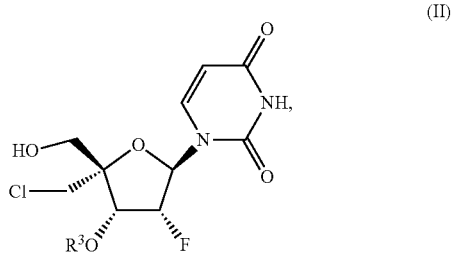

wherein $R^3$ is a trisubstituted silyl group or a triarylmethyl group.

6. The method of claim 5, wherein $R^3$ is a trisubstituted silyl group.

7. The method of claim 6, wherein the trisubstituted silyl group is selected from the group consisting of trimethylsilyl (TMS), triethylsilyl (TES), dimethylisopropylsilyl (IP- DMS), diethylisopropylsilyl (DEIPS), tert-butyldimethylsilyl (TBDMS), triisopropylsilyl (TIPS), tert-butyldiphenylsilyl (TBDPS), tri-iso-propylsilyloxymethyl, [2-(trimethylsilyl)ethoxyl]methyl, tetraisopropyldisilylene (TIPDS) and di-tert-butyldimethylsilylene (DTBS).

8. The method of claim 7, wherein the trisubstituted silyl group is a triisopropylsilyl (TIPS) group.

9. The method of claim 6, wherein the compound of formula (II) is converted to the compound of formula (JJ) by contacting the compound of formula (II) with a fluoride source.

10. The method of claim 9, wherein the fluoride source is selected from the group consisting of tetrabutylammonium fluoride, pyridine.HF, trimethylamine trihydrofluoride, hydrofluoric acid, tris(dimethylamino)sulfonium difluorotrimethylsilicate, SiF$_4$ and ammonium fluoride.

11. The method of claim 10, wherein the fluoride source is tetra-n-butylammonium fluoride.

12. The method of claim 5, wherein R$^3$ is a triarylmethyl group selected from the group consisting of trityl, monomethoxytrityl (MMTr), 4,4'-dimethoxytrityl (DMTr) and 4,4',4''-trimethoxytrityl (TMTr).

13. The method of claim 5, further comprising preparing the compound of formula (II) by hydrolyzing a compound of formula (HH) to provide the compound of formula (II), wherein the compound of formula (HH) is:

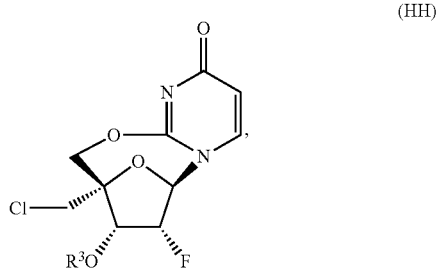

(HH)

wherein R$^3$ of (HH) is the trisubstituted silyl group or the triarylmethyl group of formula (II).

14. The method of claim 13, wherein the compound of formula (HH) is hydrolyzed with an acid.

15. The method of claim 14, wherein the acid is HCl or sulfuric acid.

16. The method of claim 13, wherein the compound of formula (HH) is hydrolyzed with a base.

17. The method of claim 13, further comprising preparing the compound of formula (HH) by chlorinating a compound of formula (GG) with a chloride source to provide the compound of formula (HH), wherein the compound of formula (GG) is:

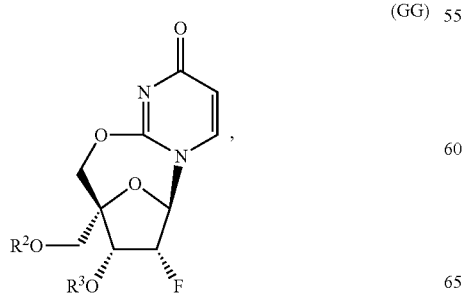

(GG)

wherein:
R$^2$ is trifluoromethanesulfonyl (Tf); and
R$^3$ of (GG) is the trisubstituted silyl group or the triarylmethyl group of formula (HH).

18. The method of claim 17, wherein the chloride source is LiCl.

19. The method of claim 17, further comprising preparing the compound of formula (GG) by contacting a compound of formula (FF) with a base to provide the compound of formula (GG), wherein the compound of formula (FF) is:

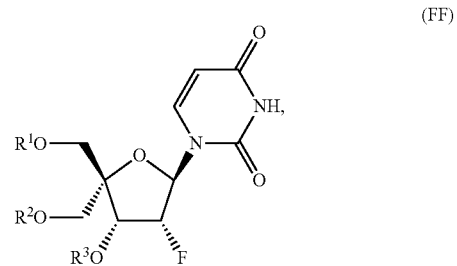

(FF)

wherein:
R$^1$ is trifluoromethanesulfonyl (Tf);
R$^2$ is the trifluoromethanesulfonyl (Tf) of formula (GG); and
R$^3$ is the trisubstituted silyl group or the triarylmethyl group of formula (GG).

20. The method of claim 19, wherein the base is an amidine reagent.

21. The method of claim 20, wherein the amidine reagent is 1,8-diazabicyclo[5.4.0]undec-7-ene (DBU) or 1,5-diazabicyclo[4.3.0]non-5-ene (DBN).

22. The method of claim 19, wherein the compound of formula (FF) is contacted with the base in a polar aprotic solvent.

23. The method of claim 19, further comprising preparing the compound of formula (FF) by triflating a compound of formula (EE) to provide the compound of formula (FF), wherein the compound of formula (EE) is:

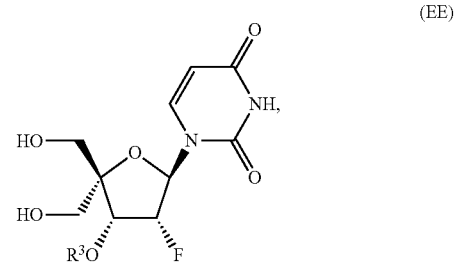

(EE)

wherein:
R$^3$ is the trisubstituted silyl group or the triarylmethyl group of formula (FF).

24. The method of claim 23, wherein the compound of formula (EE) is triflated with trifluoromethanesulfonyl halide and optionally a base or triflic anhydride.

25. The method of claim 23, further comprising preparing the compound of formula (EE) by reducing a compound of formula (DD) with a reducing agent to provide the compound of formula (EE), wherein the compound of formula (DD) is:

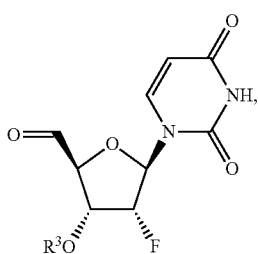

wherein:
R³ is the trisubstituted silyl group or the triarylmethyl group of formula (EE).

26. The method of claim 25, wherein the reducing agent is NaBH₄.

27. The method of claim 25, further comprising preparing the compound of formula (DD) by oxidizing a compound of formula (CC) to provide the compound of formula (DD), wherein the compound of formula (CC) is:

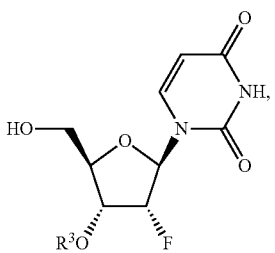

wherein:
R³ is the trisubstituted silyl group or the triarylmethyl group of formula (DD).

28. The method of claim 27, wherein the compound of formula (CC) is oxidized in the presence of oxalyl chloride, dimethyl sulfoxide, and an organic base.

29. The method of claim 27, further comprising preparing the compound of formula (CC) by removing $R^A$ from a compound of formula (BB) to provide the compound of formula (CC), wherein the compound of formula (BB) is:

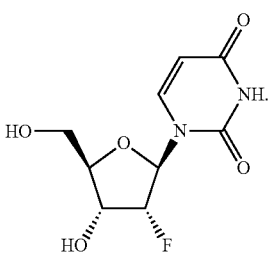

wherein:
$R^A$ is a trisubstituted silyl group; and
R³ is the trisubstituted silyl group or the triarylmethyl group of formula (CC).

30. The method of claim 29, wherein the trisubstituted silyl group is selected from the group consisting of trimethylsilyl (TMS), triethylsilyl (TES), dimethylisopropylsilyl (IPDMS), diethylisopropylsilyl (DEIPS), tert-butyldimethylsilyl (TBDMS), triisopropylsilyl (TIPS), tert-butyldiphenylsilyl (TBDPS), tri-iso-propylsilyloxymethyl, [2-(trimethylsilyl)ethoxy]methyl, tetraisopropyldisilylene (TIPDS) and di-tert-butyldimethylsilylene (DTBS).

31. The method of claim 30, wherein the trisubstituted silyl group is a triisopropylsilyl (TIPS) group.

32. The method of claim 29, further comprising preparing the compound of formula (BB) by protecting the —OH groups of a compound of formula (AA) to provide the compound of formula (BB), wherein the compound of formula (AA) is:

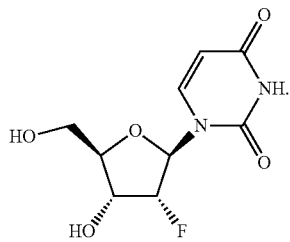

33. The method of claim 1, wherein the compound of formula (I), or a pharmaceutically acceptable salt thereof, is further crystallized in a combination of isopropyl acetate and heptane to form a crystalline form of compound (I).

34. The method of claim 1, wherein the compound of formula (I), or a pharmaceutically acceptable salt thereof, is further crystallized in a combination of methanol and water to form a crystalline form of compound (I).

35. The method of claim 33, wherein the crystalline form of compound (I) is collected by sieving.

36. The method of claim 34, wherein the crystalline form of compound (I) is collected by sieving.

37. A method of preparing a compound of formula (I):

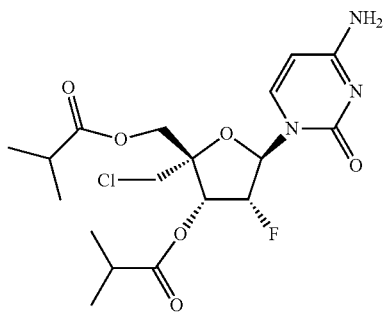

or a pharmaceutically acceptable salt thereof, comprising:
a) triflating a compound of formula (EE):

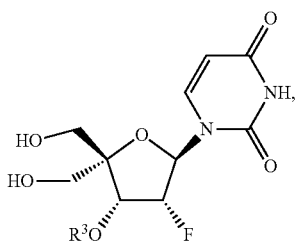

wherein R³ is a trisubstituted silyl group, to provide a compound of formula (FF):

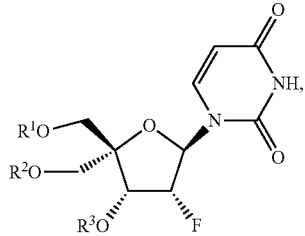
(FF)

wherein:
R¹ is trifluoromethanesulfonyl (Tf);
R² is trifluoromethanesulfonyl (Tf); and
R³ is the trisubstituted silyl group of formula (EE);

b) contacting the compound of formula (FF) with a base to provide a compound of formula (GG):

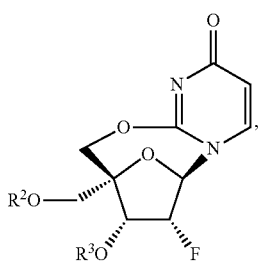
(GG)

wherein:
R² the trifluoromethanesulfonyl group of formula (FF); and
R³ is the trisubstituted silyl group of formula (FF);

c) chlorinating the compound of formula (GG) with a chloride source to provide a compound of formula (HH):

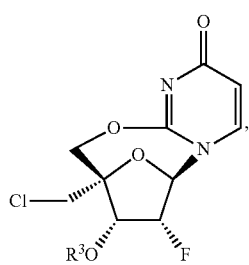
(HH)

wherein R³ is the trisubstituted silyl group of formula (GG);

d) hydrolyzing the compound of formula (HH) to provide a compound of formula (II):

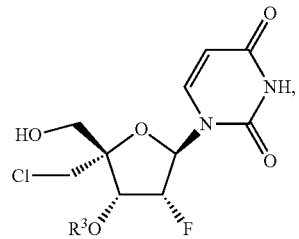
(II)

wherein R³ is the trisubstituted silyl group of formula (HH);

e) contacting the compound of formula (II) with a fluoride source to provide a compound of formula (JJ):

(JJ)

f) esterifying the compound of formula (JJ) to provide a compound of formula (KK):

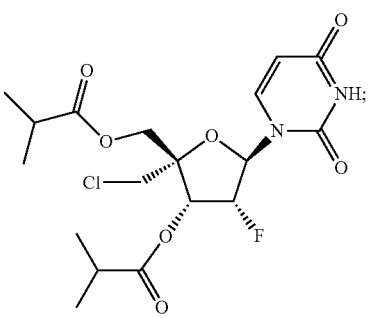
(KK)

and
g) forming a sulfonate at the 4-position of the uracil base of the compound of formula (KK); and converting the sulfonate to the compound of formula (I), or a pharmaceutically acceptable salt thereof, via aminolysis.

38. The method of claim 37, wherein the trisubstituted silyl group is selected from the group consisting of trimethylsilyl (TMS), triethylsilyl (TES), dimethylisopropylsilyl (IPDMS), diethylisopropylsilyl (DEIPS), tert-butyldimethylsilyl (TBDMS), triisopropylsilyl (TIPS), tert-butyldiphenylsilyl (TBDPS), tri-iso-propylsilyloxymethyl, [2-(trimethylsilyl)ethoxyl]methyl, tetraisopropyldisilylene (TIPDS) and di-tert-butyldimethylsilylene (DTBS).

39. The method of claim 38, wherein the trisubstituted silyl group is a triisopropylsilyl (TIPS) group.

40. The method of claim 37, wherein the fluoride source is selected from the group consisting of tetrabutylammonium fluoride, pyridine.HF, trimethylamine trihydrofluoride, hydrofluoric acid, tris(dimethylamino)sulfonium difluorotrimethylsilicate, SiF₄ and ammonium fluoride.

41. The method of claim 40, wherein the fluoride source is tetra-n-butylammonium fluoride.

42. The method of claim 37, wherein the chloride source is LiCl.

43. The method of claim 37, wherein the base is an amidine reagent.

44. The method of claim 43, wherein the amidine reagent is 1,8-diazabicyclo[5.4.0]undec-7-ene (DBU) or 1,5-diazabicyclo[4.3.0]non-5-ene (DBN).

45. The method of claim 37 further comprising oxidizing the 5'-OH group of a compound of formula (CC) followed by adding a reducing agent to produce the compound of formula (EE), wherein the compound of formula (CC) is:

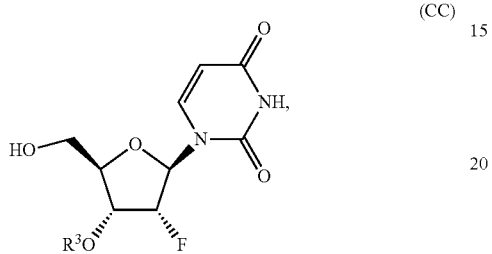

(CC)

wherein $R^3$ is the trisubstituted silyl group of formula (EE).

46. The method of claim 45 further comprising preparing the compound of formula (CC) by removing $R^4$ from a compound of formula (BB) to provide the compound of formula (CC), wherein the compound of formula (BB) is:

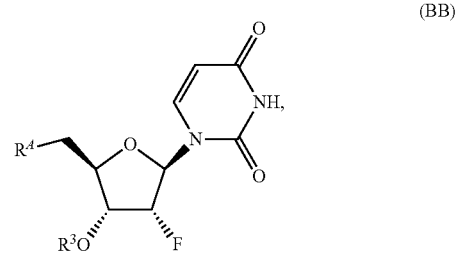

(BB)

wherein:

$R^4$ is a trisubstituted silyl group; and $R^3$ is the trisubstituted silyl group of formula (CC).

47. The method of claim 46 further comprising preparing the compound of formula (BB) by protecting the —OH groups of a compound of formula (AA) to provide the compound of formula (BB), wherein the compound of formula (AA) is:

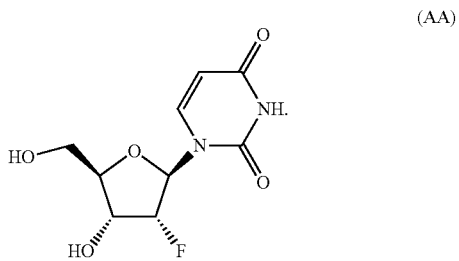 [SMILES: O=c1ccn([C@@H]2O[C@H](CO)[C@@H](O)[C@H]2F)c(=O)[nH]1]

(AA)

48. The method of claim 37, wherein the compound of formula (I), or a pharmaceutically acceptable salt thereof, is further crystallized in a combination of isopropyl acetate and heptane to form a crystalline form of compound (I).

49. The method of claim 37, wherein the compound of formula (I), or a pharmaceutically acceptable salt thereof, is further crystallized in a combination of methanol and water to form a crystalline form of compound (I).

50. The method of claim 48, wherein the crystalline form of compound (I) is collected by sieving.

51. The method of claim 49, wherein the crystalline form of compound (I) is collected by sieving.

* * * * *

UNITED STATES PATENT AND TRADEMARK OFFICE
CERTIFICATE OF CORRECTION

PATENT NO. : 10,519,185 B2
APPLICATION NO. : 15/905526
DATED : December 31, 2019
INVENTOR(S) : Vladimir Serebryany et al.

It is certified that error appears in the above-identified patent and that said Letters Patent is hereby corrected as shown below:

In the Specification

In Column 12, Line 66, delete "pyridine.HF" and insert -- pyridine•HF --, therefor.

In the Claims

In Column 21, Line 13, in Claim 10, delete "pyridine.HF" and insert -- pyridine•HF --, therefor.

In Column 23, Lines 46-58, in Claim 29, delete " 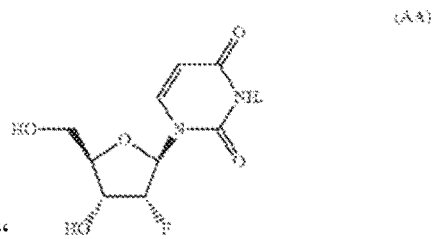 " and insert -- 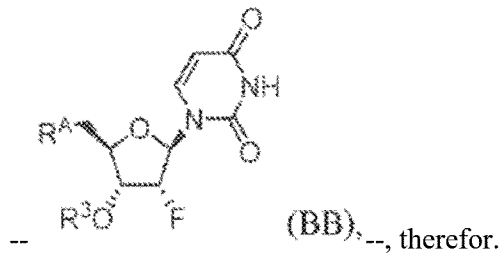 --, therefor.

In Column 25, Line 43, in Claim 37, after "R$^2$" insert -- is --, therefor.

Signed and Sealed this
Third Day of August, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)

In Column 26, Lines 20-28, in Claim 37, delete " 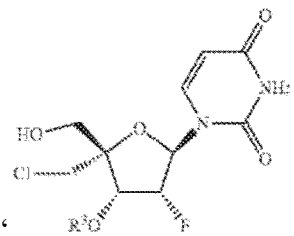 " and insert

-- 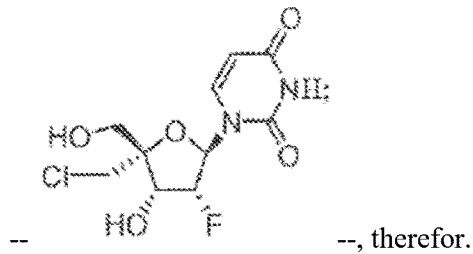 --, therefor.

In Column 26, Line 65, in Claim 40, delete "pyridine.HF" and insert -- pyridine•HF --, therefor.